(12) United States Patent
Wright

(10) Patent No.: US 9,955,975 B2
(45) Date of Patent: May 1, 2018

(54) CLAMP AND APPLICATOR

(71) Applicant: BTG International Limited, London (GB)

(72) Inventor: David Dakin Iorwerth Wright, London (GB)

(73) Assignee: BTG International Limited, London (GB)

(*) Notice: Subject to any disclaimer, the term of this patent is extended or adjusted under 35 U.S.C. 154(b) by 0 days. days.

(21) Appl. No.: 14/733,225

(22) Filed: Jun. 8, 2015

(65) Prior Publication Data
US 2016/0143642 A1 May 26, 2016

Related U.S. Application Data

(63) Continuation of application No. 13/509,383, filed as application No. PCT/GB2010/002104 on Nov. 15, 2010, now abandoned.

(30) Foreign Application Priority Data

Nov. 13, 2009 (GB) .................................. 0919950.6

(51) Int. Cl.
*A61B 17/08* (2006.01)
*A61B 17/12* (2006.01)
(Continued)

(52) U.S. Cl.
CPC ...... *A61B 17/12013* (2013.01); *A61B 17/122* (2013.01); *A61B 17/1285* (2013.01);
(Continued)

(58) Field of Classification Search
CPC .............. A61B 17/12; A61B 17/12009; A61B 17/12013; A61B 17/122; A61B 17/1222; A61B 17/128; A61B 17/1285
See application file for complete search history.

(56) References Cited

U.S. PATENT DOCUMENTS 5,601,572 A 2/1997 Middleman et al.
6,607,542 B1 8/2003 Wild
(Continued)

FOREIGN PATENT DOCUMENTS

WO 2002039913 5/2002
WO 2006082586 8/2006
WO 2009094237 7/2009

OTHER PUBLICATIONS

International Search Report dated Feb. 25, 2011; International Application No. PCT/GB2010/002104; International Filing Date: Nov. 15, 2010; 6 pages.
(Continued)

*Primary Examiner* — Jonathan Miles
(74) *Attorney, Agent, or Firm* — Blank Rome LLP

(57) ABSTRACT

The present invention provides a surgical clamp comprising a temperature sensitive shape memory material, the clamp capable of taking up a first form in which the clamp (6) is shaped to at least partially encircle a tubular structure (14); a second form shaped to substantially completely encircle the tubular structure (14) and constrict it, the clamp changing from the first form to the second form above the transition temperature of the shape memory material; and a third form derived from the first form by resilient deformation of the clamp in its first form. The present invention also provides applicators for delivering the clamps and kits comprising the clamps.

20 Claims, 8 Drawing Sheets

(51) Int. Cl.
    *A61B 17/122*     (2006.01)
    *A61B 17/128*     (2006.01)
    *A61B 90/92*     (2016.01)
    *A61B 17/00*     (2006.01)
    *A61B 90/00*     (2016.01)

(52) U.S. Cl.
    CPC .... *A61B 90/92* (2016.02); *A61B 2017/00867* (2013.01); *A61B 2017/00871* (2013.01); *A61B 2090/0811* (2016.02)

(56) References Cited

U.S. PATENT DOCUMENTS

| | | |
|---|---|---|
| 6,783,004 B1 | 8/2004 | Rinner |
| 2006/0178679 A1 | 8/2006 | Richter |
| 2007/0118162 A1 | 5/2007 | Abi-Kheirs |
| 2008/0051829 A1 | 2/2008 | Eidenschink et al. |

OTHER PUBLICATIONS

Written Opinion dated Feb. 25, 2011; International Application No. PCT/GB2010/002104; International Filing Date: Nov. 15, 2010; 9 pages.

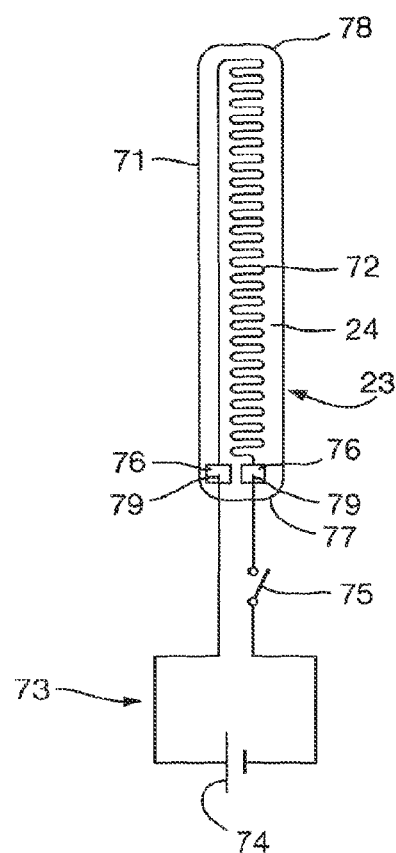
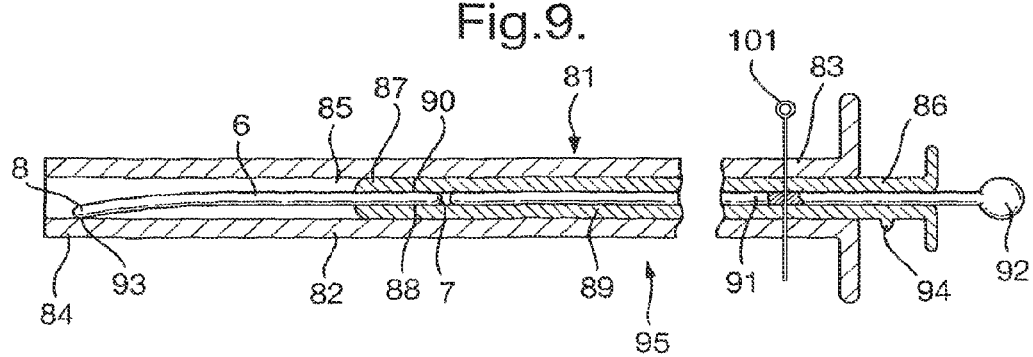

CLAMP AND APPLICATOR

RELATED APPLICATIONS

This application is a continuation of U.S. patent application Ser. No. 13/509,383, filed May 25, 2012, which is a 371 application extending from International Application No. PCT/GB2010/002104, filed Nov. 15, 2010. The above-referenced applications are incorporated herein by reference.

The present invention is made in the area of surgical clamping devices for the clamping of tissues and particularly for the constriction and closing of tubular structures such as blood vessels and ducts within the body. Particularly the present invention makes use of the properties of temperature sensitive shape memory materials to provide, preferably permanent, clamping or constriction devices. These surgical clamps are suitable for use where minimally invasive surgery is preferred, for example where there is no hollow viscus or space such that direct visualisation via endoscopic equipment is not possible. Such devices are particularly useful in the clamping of varicose veins.

The use of various types of clamp for closing of blood vessels during surgery is well known. Several of these devices use the properties of shape memory materials to achieve the closure of the device. For example U.S. Pat. No. 5,282,812 provides surgical clamps for the temporary occlusion of a blood vessel, formed from a material having positional memory. U.S. Pat. No. 6,746,461 describes blood vessel clamps in which the jaws of the clamp are attached by a shape memory material hinge. The hinge is set to bend at a predetermined angle when subjected to body temperature and so clamp the blood vessel. Such clamps are not suitable for use in restricted situations because of their size, or the tools required to apply them and they are not intended to be permanent.

U.S. Pat. No. 6,001,110 describes hemostatic gastric clips having pseudo elastic properties at body temperature. The clips are deployed without the application or removal of heat, and the clips transition to the closed state following the removal of stress at body temperature. The clips are designed to be operated using an endoscope.

U.S. Pat. No. 5,601,572 describes various devices using shape memory material having pseuoelastic properties rather than thermal shape memory. The devices include a ring clip and a device for delivering the clip. The clip is a circular shape when not subject to mechanical stress and a straightened shape when subjected to mechanical stress and retained in the delivery device. These devices are not intended as clamps for tubular structures and do not constrict blood vessels.

WO2005037138 provides external aneurysm supports comprising shape memory materials. The support may be delivered to the anurism in a rolled up form and is applied to the anurism is a second form.

WO06/011127 provides a variety of surgical devices comprising shape memory materials displaying a stress retained Martinsitic state including an anastomosis ring clip.

WO2007146456 provides spring clips for reducing or stopping blood flow to fibroids.

US2006/0149348 describes net-like compression sleeves for the local enclosure of a blood vessel. These structures prevent dilation of the respective vessel section, or if already dilated, return the blood vessel to its original state. They may be fabricated from shape memory material such as Nitinol. In this case the shape memory may be super elastic or thermal.

In situations where there is little space in which to work, it is important that the clamps used are easy to place and/or adjust in a confined space and take up minimal space when fitted. It is desirable that applicators used to deliver and place the clamp should be minimally invasive and able to deliver and place the clamp without the use of open surgery. Since visualisation of the site is often difficult in minimally invasive surgery, it is also desirable that such clamps should be easily visualised by other means, for example by ultrasound.

Shape memory material clamps which transition between two forms, that is to say, from a first form in which the clamp is delivered directly to a second form which clamps a structure, are difficult to manipulate in practice, especially in confirmed spaces. Changes in shape from the delivery form to the clamp form can be rapid, leaving no time to adjust the position of the clamp. Further, since the clamp and applicator tend to warm up during use shape change can occur immediately on exit from the applicator adding to the problem of positioning the device.

The clamps and devices described herein overcome these issues by providing a clamp transitioning between three shapes or forms vis: a form suitable for delivery, such as a linearised or straight form, in which the clamp is found within the delivery device, a further form in which the clamp is able to (at least partially) encircle a structure but does not clamp it, so that the clamp can be adjusted in position, and a further form in which the clamp constricts the structure to close it, once positioned.

The present invention provides an applicator for a surgical clamp comprising a housing with an inner chamber a surgical clamp within the inner chamber and a means for moving the surgical clamp out of the inner chamber, the surgical clamp comprising a shape memory material and capable of assuming:
  a first form in which the clamp is shaped to at least partially encircle a tubular structure;
  a second form in which the clamp is shaped to substantially completely encircle the tubular structure and to constrict it, and
  a third form derived from the first form by resilient deformation of the clamp in its first form and adoptable within the applicator chamber,
clamp induced to change from the first form to the second form on exposure to a temperature above the transition temperature of the shape memory material.

The clamp therefore has three forms. In the third form the clamp is adapted to fit within the inner chamber of the housing, and is preferably a linearised, (i.e. straightened or unrolled), version of the first form. It is preferably straight or slightly curved, and this allows it to be easily delivered to the tissue to be clamped. This linear form allows it to be placed in the chamber of the applicator, where it is constrained to remain in the third form by the walls of the inner chamber. The third form is derived by resilient deformation of the first form, so the clamp is able to return substantially to the first form, and so returns to the first form when moved out of the applicator chamber, which is open to the exterior at the distal end. The first form is shaped to at least partially encircle a tubular structure and so is typically curved. This allows the clamp to pass easily around the structure to be clamped as it leaves the applicator chamber, whilst requiring minimal space to do so and allows the clamp to be placed on the structure to be clamped without the use of additional implements. The applicator therefore serves both to deliver the clamp to the site of the tissue and to assist in placing the clamp onto the tissue. The clamp in the first form can be adjusted in position at this point since it does not clamp the structure.

The clamp in the first form is induced to change from the first form to the second form (in which the clamp is shaped to substantially completely encircle the tubular structure and to constrict it) on exposure to a temperature above the transition temperature of the shape memory material, for example by exposure to the body temperature of the patient. As the clamp takes up its second form it completely encircles the structure and constricts it, thereby clamping the structure.

The applicator housing is preferably a tubular member having a lumen, the lumen having proximal end, and a distal end. The lumen provides the inner chamber of the housing, the surgical clamp being within the lumen.

Thus in one embodiment of the invention an applicator comprises a tubular member having a proximal end and a distal end and a lumen, a surgical clamp of the invention within the lumen and a means for moving the clamp out of the distal end of the lumen. The tubular member is preferably straight, but may be curved along its long axis to facilitate access to the structure to be clamped. The lumen of the tubular member may be round in cross section, but can be shaped to hold clamps of various cross sections and thereby provide predictable orientation of the clamp as it exits the applicator. The lumen of the tubular member extends from the proximal to the distal end and is typically open at least at the distal end.

The distal end of the tubular member may be shaped to aid tissue penetration and dissection of the structure, free from the surrounding tissues, for example by forming it into a point or blade.

The means for moving the clamp out of the inner chamber is preferably a plunger or rod, moveable within the inner chamber of the housing. The moving means is preferably operable from the proximal end of the applicator to move the clamp out of the distal end of the inner chamber of the applicator.

In one advantageous embodiment the distal end of the moving means releasably engages the clamp. This allows adjustment of the position of the clamp, such as movement of the clamp back and forth, or rotationally, within the applicator chamber. This allows the position of the clamp to be adjusted during the procedure in order to assist placement. In this embodiment the applicator preferably also comprises an ejection means for releasing the clamp from the moving means which is preferably operable from the proximal end of the applicator. The means for releasably engaging the clamp may be for example a cut out in the distal end of the moving means, into which the proximal end of the clamp fits. The ejection means is for example a rod passes through the long axis of the plunger which is operable to eject the clamp from the cut out.

The clamp of the invention is held within the chamber of the applicator, but since it has been resiliently deformed, from the first form, it tends to return to this form as it is moved out of the chamber. It may not be immediately obvious, by looking at the applicator, which way the clamp will begin to curve as it leaves the chamber. It may be necessary therefore for the applicator or the clamp itself to comprise an indication identifying the direction in which the clamp will begin to curve once it leaves the chamber. It is preferable that this indication is visible when the applicator is inserted into the operation site, and the distal end is therefore not visible. This can be achieved by providing an indication visible from the outside of the applicator to identify the direction. Thus the applicator may be marked at the proximal end to indicate the direction of curve, for example on the proximal part of the housing or tubular member, or the means for moving the clamp out of the chamber may comprise an indication. It is particularly useful for the moving means to comprise an indicator when the means for moving the clamp out of the chamber reversibly engages the clamp, since in this way the orientation of the moving means is fixed to the orientation of the clamp.

Where the clamp itself is provided with an indication, it could be marked e.g. by colouring one surface to indicate the direction of curve. A further advantage of providing a coloured clamp is that coloured clamps may be more easily visible, should they need to be recovered from inside the body. It may therefore be advantageous for the clamp to be coloured in a way easily visible inside the body, for example one surface may be coloured blue.

In a further method to provide an indication visible from the outside of the applicator, the applicator may comprise a portion through which the orientation of the clamp can be identified. For example the applicator housing or tubular member, may comprise a transparent portion through which the orientation of the clamp can be identified. In one embodiment the housing or tubular member is transparent The applicator may also comprise a means for preventing inadvertent ejection of the clamp from the inner chamber. This may take the form of a locking means for preventing the moving means from moving the clamp out of the inner chamber, until required. Such a locking means may be a pin passing through the moving means or through both the moving means and the housing or may be a detachable lateral extension of the moving means, which when present, prevents the moving means from ejecting the clamp. A simple cap covering the distal end of the applicator may also be used. This not only prevents the clamp from being inadvertently ejected from the inner chamber, but protects the distal end of the applicator and assists in maintaining sterility. This is especially appropriate if the distal end is formed into a blade or point as described above.

Because of their sensitivity to heat, the clamps and applicators comprising them cannot be sterilised by heat. It is preferred, therefore, that they be sterilised by chemical or radiation means.

The applicators of the invention (excluding the clamp) may be manufactured from any material appropriate for surgical implements, such as for example, stainless steel or plastic.

The clamp comprises a temperature sensitive shape memory material, which enables it to change from the first form to the second form above the transition temperature. In some embodiments, the clamp is fabricated completely of shape memory material, that is, the clamp consists of shape memory material. In other embodiments the clamp comprises a shape memory material but may also comprise materials that provide additional properties. For example the clamp may comprise portions or elements that provide additional resilience, heating means and/or coatings.

Shape memory materials have a stable form and can be made to take up a different, unstable form. Temperature sensitive shape memory materials can be induced to change from the unstable form to the stable form above a particular temperature referred to as the transition temperature.

Shape memory materials, such as nickle titanium alloys, have a stable, Austenitic form and can be made to take up a different, unstable, Martensitic form. Temperature sensitive shape memory materials can be induced to change shape when exposed to a temperature above that at which the temperature-unstable Martensitic form of the material reverts to the temperature-stable Austenitic form. The temperature at which the transition from the Martensitic form to Austenitic form occurs is known as the transition temperature. Since the transition occurs over a range of temperatures depending on the alloy, the point at which the transition begins As is a more precise measure, and it is this temperature that is referred to herein as the transition temperature. The composition of the material can be adjusted to provide a material having a transition temperature within a desired range and thus to transform in shape at an appropriate temperature or over an appropriate temperature range. Such compositions and methods of making them are well known in the art. Thus the first form of the clamp the shape memory material is substantially in the Martensitic form, and in the second form of the clamp the shape memory material is substantially in the Austenitic form. Materials of this type and clamps made from them, can therefore be adapted to take up two predefined forms and can transition between predefined Martensitic and Austenitic forms by the application of heat. Once in the Austenitic form the transition is complete and the clamp will not return to the Martensitic form unless deformed.

The shape memory material of the clamp is preferably a shape memory alloy but may also be a shape memory polymer. The shape memory material is preferably a nickle titanium alloys, such as Nitinol.

In one embodiment the shape memory material has a transition temperature which is less than normal body temperature, so that it changes from the first form to the second form when exposed to normal body temperature, although it can be held in the first form at temperatures below this. The transition temperature is typically between 10° C. and J7° C. Transition temperatures below body temperature are particularly preferred in cases where the temperature of the operation site can be held below body temperature, for example by the use of a cooled, degassed saline perfusion. This approach allows the use of clamps in which the transition temperature of the shape memory material is for example between 10° C. and 30° C. However, such clamps require more careful storage. Preferably the transition temperature of the material is between 20° C. or 25° C. and 37° C. Clamps in which the transition temperature of the shape memory material is between 30° C. and 37° C. are preferred.

In a further embodiment, the transition temperature for the shape memory material is above body temperature, so that a temperature above body temperature is required for the clamp to transition from the first form to the second form. Such clamps are less susceptible to inadvertent changes in form during manufacture, storage, or transit. Usefully the transition temperature for these clamps will be at least 38° C., and preferably at least 40° C. in order to avoid inadvertent change of form at temperatures close to body temperature which might occur during handling. Generally, in order to avoid tissue damage, the transition temperature in this embodiment is typically no more than 45° C., but may be up to 50° C. However, where transition from the first form to the second form is rapid, where exposure of local tissues to heat is brief, where local heating does not present a problem, or where temperature increases can be kept sufficiently localised to minimise damage to surrounding tissues, higher transition temperatures, for example between 51° C. and 65° C., may be tolerated. Clamps of this form have the added advantage that they are even less sensitive to temperature changes in the environment during manufacture use, storage and transport. Thus clamps of this type have transition temperatures between about 38° C. and about 65° C., Advantageously the transition temperature may be between 38 and 50° C., however where higher temperatures are tolerated the transition temperature may usefully be between 50° C. and 65° C.

The clamp is preferably generally elongate when linearised e.g. in its third form. This, inter alia, allows the use of narrow introducers which are more convenient in areas where access is difficult. The clamp has two ends, a proximal end and a distal end, and two faces, an inner face oriented towards the clamped structure when installed and an outer face, oriented away from the clamped structure. The clamp may be formed, for example, from wires or rods of various cross sections or may be laminar. At least one of the proximal or distal ends may be shaped to allow ease of passage around the tissue to be clamped, for example by being radiused.

In the first form, the clamp is shaped to at least partially encircle a tubular structure and so is generally curved. The internal diameter of the clamp being defined as the diameter of the largest cylinder that the clamp encircles in that form. The clamp may be of any shape that is suitable to at least partially encircle a tubular structure, however a ring shape a "U", "C" or "J" shape or a closed cylinder or an open cylinder (where the proximal and distal ends of the clamp do not meet) or a spiral or helical shape is convenient. Where the clamp is in the form of a lamina, forming an open or closed cylinder, the lamina may comprise a plurality of open areas so that it resembles a mesh. In this form, tissue growth within the spaces serves to assist adhesion of the clamp and maintain it in position. Never the less, a lamina, in which there are few, or no, open areas is more convenient when positioning the clamp since this prevents inadvertent snagging of surrounding tissue.

In one advantageous embodiment, the transverse cross section of the clamp is such that the force exerted on transition from the first form to the second form is focussed on a small area. To this end the clamp may, for example, be of convex or V shaped or triangular form in cross section, or may have a plurality of raised portions, for example in the form of ridges or projections on its inner face. These features provide an improved local crushing of the tissue in order to promote closure of the lumen and aid in positioning the clamp before closure.

In the first form the clamp is shaped to at least partially encircle the tubular structure and remain in place whilst it is positioned, thus it is preferred that the clamp encircles the tubular structure around which it is to be placed, at least to the extent that the clamp remains in position around the tubular structure, however, it preferably does not deform the tubular structure, and is free to move. In this way, once in position, the clamp can be manipulated easily in order to adjust its final placement, before it takes up the second form. It is preferable that the clamp substantially encircles the structure, preferably to the extent that the distance between the proximal and distal end of the clamp are sufficiently close to prevent the structure slipping out. The clamp is thereby loosely attached to the structure. The distance between the proximal and distal ends of the clamp, (measured as the shortest distance between the proximal and distal extremities of the clamp) in the first form is preferably less than the diameter of the vessel upon which the clamp is to be placed. Typically the opening will be less than about 80% of the internal diameter of the clamp itself and preferably less than about 60% of the internal diameter of the clamp. In general the opening will be small with the distance between proximal and distal ends of the clamp being less than 50, less than 40, less than 30 or less than 20% of the internal diameter, and preferably less than 10%. In helical forms it is preferred that in the first form at least 75% of one turn is formed, preferably, the proximal and distal ends of the clamp overlap, so that at least one turn of the helix has been made Preferably the clamp in the first form is shaped to substantially or completely encircle a tubular structure. Preferably it is a closed shape, such as a ring, ellipse or cylinder or forms a spiral or helix. It is preferable therefore that the proximal and distal ends of the clamp approximately meet or overlap in the first form.

In one embodiment, the clamp in the first form is sized according to the diameter of the tubular structure upon which it is to be placed. In order to facilitate adjustment of the position of the clamp in the first form, its internal diameter should not be smaller than the diameter of the tubular structure upon which it is intended to be placed. The smallest internal diameter of the clamp in the first form will preferably be no more than 50% greater than that of the structure upon which it is to be placed. Preferably it is no more than 25% greater.

In an alternative embodiment, one clamp in the first form will be suitable to clamp a variety of tubular structure diameters. This is especially the case where the final diameter required of the second form will be the same in all cases.

In the second form the clamp is shaped to constrict a tubular structure to close or at least partially restrict the lumen, thus preferably it completely encircles the tubular structure and constricts it. The clamp in the second form therefore has a second internal diameter, which is smaller than that of the clamp in the first form. In this manner the clamp shrinks in size, takes up less space and does not leave portions protruding into the surrounding space, which could cause tissue damage later. Furthermore approximately equal force is applied in constriction around the structure. Never the less, in some circumstances it may be acceptable for the lumen of the structure to be deformed by side to side compression, by torsion or by bending of the structure, by appropriate design of the second form. Typically the clamp in the second form has an internal diameter of less than about 90% of the clamp in the first form. However, a variety of clamps having different internal diameters in the second form are envisaged thus it is envisaged that clamps with an internal diameter in the second form that are less than 85, 80, 75, 70, 65, 60, 55, 50, 45, 40, 35, 30, 25, 20, 15 and 10% of the diameter of the first form are envisaged.

Preferably the clamp in the second form restricts the lumen of the tubular structure to the extent that the lumen is functionally closed (i.e. no longer serves its purpose) or is completely closed. For blood vessels this would be the case when the vessel is closed or is squeezed sufficiently tightly so as to squeeze out the collagen matrix, leaving only collagen fibres. Preferably there is no opportunity for recanalisation.

In the second form the internal diameter of the clamp may be reduced in several ways. In open ring forms, the ring is closed to constrict the tubular structure, in helical forms (in which the proximal and distal ends of the clamp overlap side by side) the overlap becomes greater, in spiral forms (in which the proximal and distal ends overlap in an over and under fashion) the spiral becomes tighter, whilst in closed ring forms the proximal and distal ends of the clamp become overlapped, or they are further overlapped in order to reduce the internal diameter and thereby constrict and close the tubular structure. When the clamp forms a cylinder in the first form, the ends may overlap each other in an over and under fashion, in a side by side fashion or by interdigitation of finger-like projections on the proximal or distal ends, for example.

In one embodiment the free ends of the clamp may interlock for greater strength.

In wire clamps, the internal diameter of the clamp in the first form may also be reduced by deformation of one or more portions of the wire. This can be achieved, for example if two lengths of the wire are twisted together to form a twisted pair. In this embodiment it will generally be necessary to stabilise the ends of the clamp to prevent the clamp opening. Accordingly, it is preferred that at least the proximal and distal portions of the wire should be twisted together.

In the third form the clamp is adapted to fit within the inner chamber of the housing, and is preferably a linearised, (i.e. straightened or unrolled), version of the first form. In this form the clamp is elongate and is preferably straight or slightly curved, and this allows it to be easily delivered to the tissue to be clamped. This linear form allows it to be placed in the chamber of the applicator, where it is constrained to remain in the third form by the walls of the inner chamber.

The clamps of the invention transition from the first form to the second form when heated to a point where transition occurs. The transition temperature may be below or above body temperature. In one advantageous embodiment the clamp comprises heating means for heating the clamp to the point where transition occurs. Such clamps do not rely on body heat for transition between forms and may have higher transition temperatures.

Thus a further embodiment of the invention provides a surgical clamp for constricting a tubular structure within the body, comprising a shape memory material, and a heating means for heating the shape memory material.

The heating means in clamps of the invention may be provided with energy directly, for example by an electrical connection to the heating means, providing, for example a diathermy current, or indirectly by a source providing radiofrequency microwave or ultrasound energy. For example the clamp may comprise a portion that is susceptible to heating by microwave or ultra sound energy, it may comprise an inductive portion which is part of an electromagnetic oscillation circuit or it may comprise a resistive heating element.

Conveniently, where the temperature of the shape memory material is raised by electrical heating means, current can be delivered via the applicator, for example through the means for moving the clamp from the housing chamber. The current causes resistive heating of the clamp, raising its temperature above the transition temperature and causing the clamp to change form, from the first form to the second form. In such circumstances it may be necessary for the applicator to be electrically insulated from the body.

In such clamps, the transition temperature is not required to be below normal body temperature (37° C.) and may be greater, thus in addition to the preferred ranges already described the transition temperature may be, for example at least 40° C. In some instances the transition temperature may be higher and transition temperatures of greater than or equal to 45, 50, 55 or 60° C. are envisaged, since high temperatures are used for only a short time and are very localised. Such clamps are less susceptible to temperature fluctuations in production, transport, storage and use. The maximum transition temperature of these clamps would be no higher than that which tends to cause local tissue damage and in any case not greater than 65° C. since higher transition temperatures are unnecessary to provide stability of the clamp to temperature fluctuations, under normal circumstances.

In a further embodiment, the present invention provides a surgical clamp as described above. The clamp comprising a shape memory material, said clamp capable of assuming:
- a first form in which the clamp is shaped to at least partially encircle a tubular structure, the clamp being in the first form below the transition temperature of the shape memory material,
- a second form shaped to substantially completely encircle the tubular structure and to constrict it, the clamp changing from the first form to the second form above the transition temperature of the shape memory material.
- A third linear form derived from the first form by resilient deformation.

The current invention also provides a method of clamping a structure, such as a vein or artery, in the body of a subject, such as a human or animal patient, comprising applying to the structure a clamp as described herein. Particularly, the method comprises
(i) providing a clamp comprising a shape memory material, the clamp capable of assuming:
- a first form in which the clamp is shaped to at least partially encircle said tubular structure;
- a second form shaped to substantially completely encircle the tubular structure and to constrict it, the clamp induced to change from the first form to the second form above the transition temperature of the shape memory material,
- a third form derived from the first form by resilient deformation of the clamp in its first form, the clamp being provided in the third form, (b) applying the clamp to the structure whilst allowing the clamp to return to the first form; and
(c) raising the temperature of the shape memory material to a temperature at which it changes to the second form, thereby clamping the tubular structure.

The clamps of the invention are particularly suited to procedures in which the temperature of the operation site or structure to be clamped is below the transition temperature of the shape memory material during placement of the clamp. This can be achieved either by cooling the operation site or structure or by using a clamp comprising a shape memory material with a transition temperature above the patient's body temperature (usually 37° C.).

By bathing the structure to be clamped in a fluid, particularly a degassed fluid, such as degassed saline, the progress of the procedure can be followed easily by ultrasound. The fluid can also be used to aid dissection of the surrounding tissues away form the structure to be clamped. Anaesthetic may also be added to the fluid. The temperature of the structure to be clamped can be controlled by controlling the temperature of the fluid.

The fluid may be cooled to a temperature below the patient's body temperature, which assists placement of the clamps by preventing those with lower transition temperatures from transitioning to the second form too quickly. This approach is particularly suitable when the transition temperature of the shape memory material is close to body temperature.

In one embodiment the temperature of the shape memory material is raised by exposure to the patients body, for example by removal of the cooled fluid.

Alternatively, the clamp applied to the tissue can be exposed to fluid at a temperature suitable to induce transition, for example by flushing the area with fluid at a suitable temperature, that is to say at or above the transition temperature.

Thus, in one approach, the structure to be clamped is bathed in a fluid below body temperature during placement of the clamp. After placement of the clamp the temperature of the shape memory material is raised to a temperature at which the clamp transitions to the second form e.g. by either, removing the fluid or by increasing the temperature of the fluid. This is particularly suitable where the transition temperature of the shape memory material is at or below body temperature.

In another approach the transition temperature of the shape memory material is above body temperature and the temperature of the shape memory material is raised to a temperature at which the clamp transitions to the second form by flushing the operation site with fluid at a suitable temperature.

Where the shape memory material has a transition temperature higher than body temperature, it may not be necessary to cool the bathing fluid, (or to provide a bathing fluid at all) however in order to bring about transition of the clamp the temperature of the clamp is raised, and this may be achieved by providing a bathing fluid at a suitable temperature.

It is advantageous to provide the current clamps as part of a kit. Such clamps may be provided individually in any of the three forms that the clamp may assume, however, it is preferable for the sake of convenience to provide the clamp in either the first form or the third form and most conveniently in the third form. It is preferred that the clamp be provided sterile. Thus the current invention also provides a kit comprising a clamp of the invention. Kits preferably comprise at least two clamps which may be of different sizes, allowing the surgeon to choose one of appropriate size as required. The kit may comprise a set of clamps selected for use in a procedure requiring more than one clamp, so that clamps for each structure to be clamped during the procedure are available in one kit.

As part of a kit or otherwise, if clamps are provided in the third form, then it is preferred that they are provided as part of an assembly that maintains the clamp in the third form, by restraining it from returning to the first form. The assembly typically comprises a clamp of the invention in the third form and a means for holding the clamp in the third form. The clamp may for example be held in a tubular member, whose inner walls restrain the clamp from returning to the first form or may be held in a cartridge containing several clamps held in the third form.

Conveniently the clamp may then be transferred from the assembly to an applicator of the invention. Alternatively the assembly itself may form part, or all, of an applicator of the invention. For example the assembly may comprise part, or all of the applicator housing, or the tubular member. In this manner the applicator, excluding the assembly incorporating the clamp, may be re-usable, whilst the remainder of the assembly following placement of the clamp, is disposable.

Whether as part of a kit or otherwise, it is advantageous to provide clamps of a plurality of different sizes. It is advantageous therefore, to provide a coding system to indicate the size of the clamp or the size of the structure for which it is suitable. Thus the clamps may be identified according to their size, or the size of the structure for which it is suitable, for example by a colour coding, which may be placed on the clamps, on the applicator, on the assembly referred to above, or in any other manner that associates the colour with the clamp of a particular size or the size of the structure for which it is suitable.

The clamps and applicators of the invention may be conveniently used in a number of circumstances. For example closure of blood vessels such as veins qr arteries, or smaller vessels, closure of tubes such as fallopian tubes, bile ducts and vas deferens, narrowing veins to make pseudo valves and restoring the function of incompetent valves.

The present invention will now be described further with reference to the following non limiting examples schemes and figures. Further embodiments falling within the scope of the invention will occur to those skilled in the art in the light of these.

FIGURES

FIG. 1 shows an applicator of the invention in general view in longitudinal section.

FIG. 2a shows the applicator in proximity to a blood vessel. FIG. 2b shows a clamp urged from the distal end of the applicator. FIG. 2c shows clamps in place around a blood vessel in the first form and FIG. 2d shows a clamp in the second form where the blood vessel has been permanently constricted to close the lumen.

FIG. 3 illustrates a further embodiment of the applicator for surgical clamps

FIGS. 4a to 7a show the clamp in the first form, FIGS. 4b to 7b show the clamp in the first form attached to a blood vessel, FIGS. 4c to 7c show the clamps in the second form and FIGS. 4d to 7d show the clamps in the second form attached to a blood vessel. FIG. 4e is an end on view from P. FIG. 7e is a cross section through the blood vessel at A-A' showing the blood vessel closed and FIG. 7f is an end on view from P.

FIG. 8 shows a clamp which incorporates a means for heating the shape memory material to a temperature above the transition temperature.

FIG. 9 illustrates an applicator in which the clamp is reversibly engaged with the plunger for easier manipulation.

Figure 1:
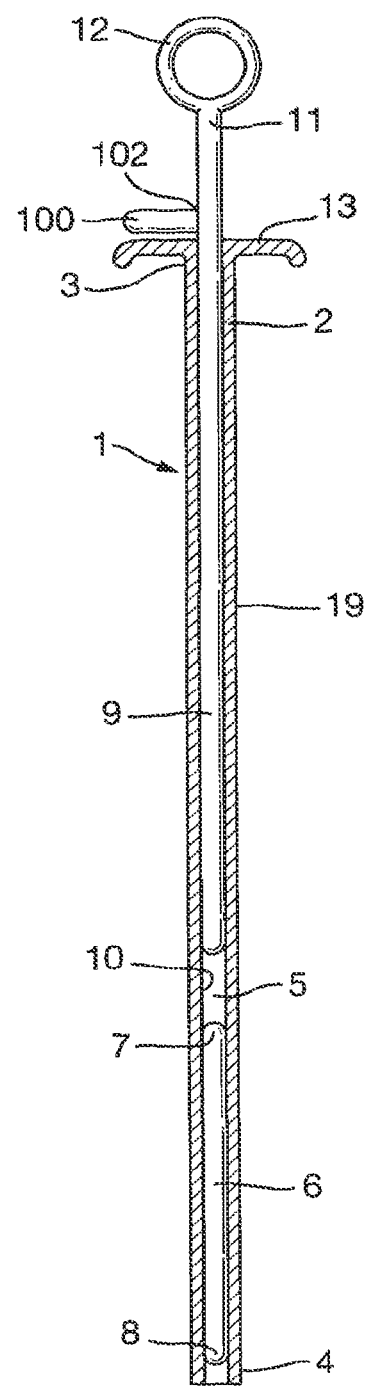

FIG. 1 shows an applicator of the invention m general view (1). The) applicator has a housing illustrated generally at (2) acting as an introducer. The housing comprises a straight tubular member (19) and has a proximal end (3) and a distal end (4) and an inner chamber which is the lumen (5). A surgical clamp, in the third, linear, form (6) is within the lumen (5) and has a proximal end (7) and a distal end (8).

A moving means in the form of a plunger (9) is movable within the lumen of the tubular member (5) and is of sufficient length to move the clamp (6) out of the distal end of the tubular member (4) when pushed into the lumen (5). The clamp (6) within the lumen (5) cannot return to the first form because it is constrained by the inner wall (10) of the tubular member. The plunger is manipulated from its proximal end (11) using the grip (12) whilst the applicator has means to steady the implement in the form of grips, shown at (13). The proximal end of the plunger also incorporates a lateral extension (100) which prevents the plunger moving into the lumen. The lateral extension comprises a weak point (102) at which the extension can be broken off to allow forward movement of the plunger. This prevents accidental ejection of the clamp until required.

Figure 2A:
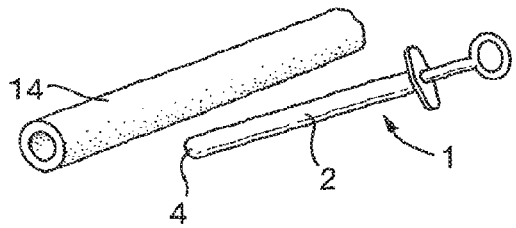
Figure 2B:
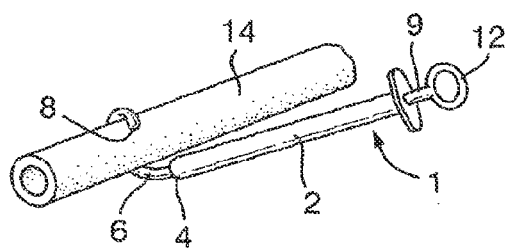
Figure 2C:
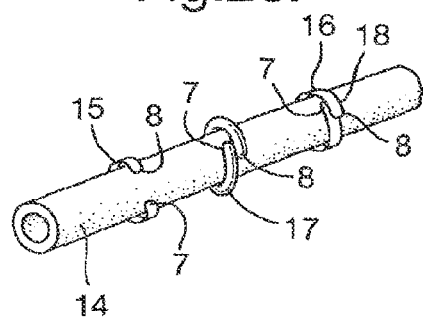
Figure 2D:
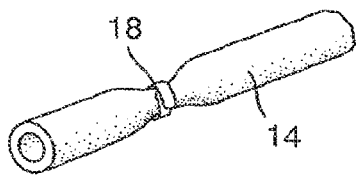

FIGS. 2a to 2d illustrate the installation of the clamp. FIG. 2a shows the applicator (1) in preparation for installing the clamp. The distal end (4) of the housing (2) is brought. into proximity with a blood vessel (14). In FIG. 2b the clamp (6), in its third form, is urged out of the distal end of the housing (2) by moving the plunger (9) forward. As the clamp (6), in its linearised, third form leaves the distal end of the housing (4) it begins to return to the curved, first form and the distal end of the clamp (8) is guided around the blood vessel (14). FIG. 2c shows three clamps (15, 16 & 17) attached to the blood vessel (14). The clamps are in the first form. One clamp (15) forms an open ring in which the proximal (7) and distal (8) ends of the clamp do not meet, however, the gap between them prevents the blood vessel (14) slipping out. The clamp is free to move on the blood vessel and may be adjusted for final positioning. The clamp (16) is also in the first form, however, in this clamp the proximal (7) and distal (8) ends overlap (18) in an "over and under" fashion. The third clamp (17) has proximal (7) and distal (8) ends overlapping side to side. FIG. 2d shows a clamp in the second form (18) after the temperature of the memory material has been raised above the transition temperature. The internal diameter of the clamp has been reduced and the clamp has become tightly wrapped around the blood vessel (14) constricting it and sealing off the vessel.

Figure 3:
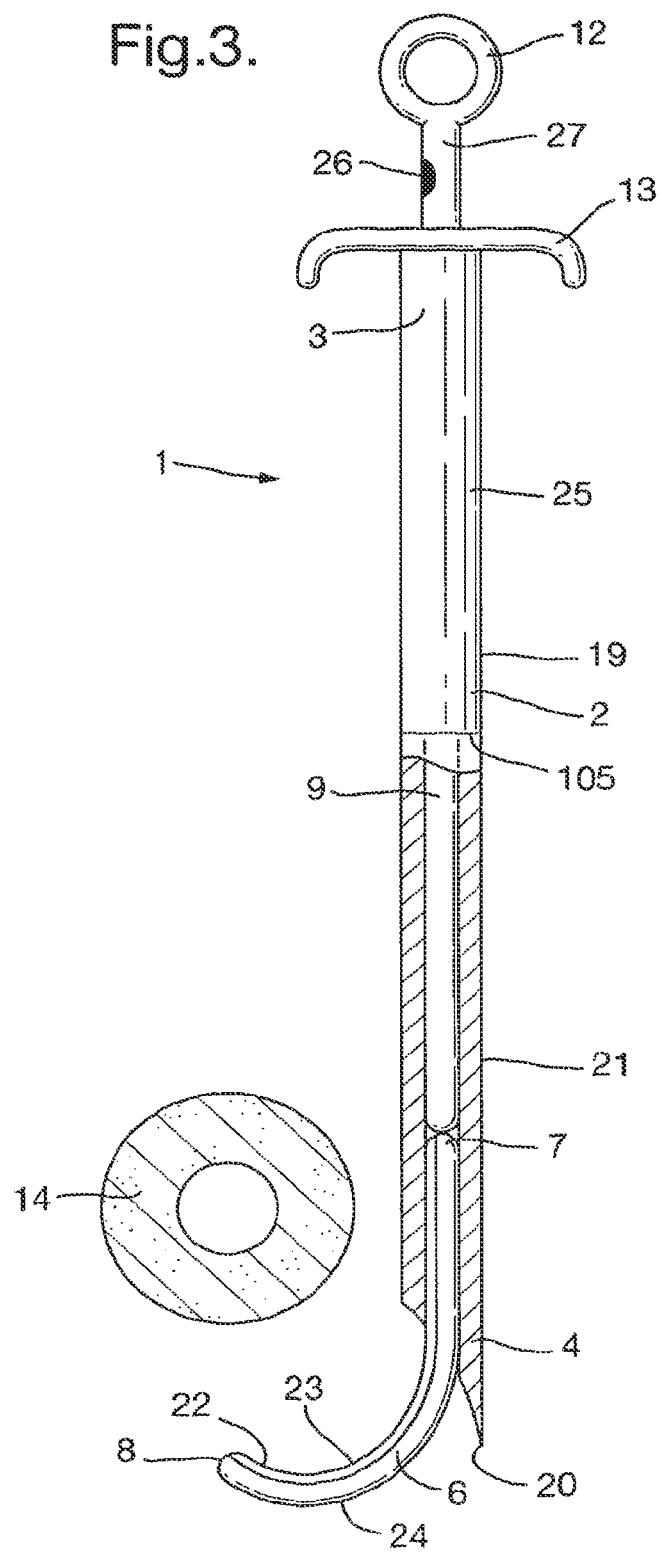

FIG. 3 illustrates a further embodiment of the applicator (1) in which the housing (2) comprises a portion through which the clamp (6) can be seen (21). In this case this is a transparent portion. The transparent portion extends around the whole circumference of the tubular member (19), and extends from a point level with the proximal extent of the clamp (before use) (105) to the distal portion of the tubular member (4), so that the distal end of the applicator is transparent. The clamp can therefore be easily seen within the lumen. The clamp has a proximal end (7) and a distal end (8), a inner face (23), which, when the clamp is attached to the blood vessel, is oriented towards the blood vessel (14) and an outer face (24) oriented away from the blood vessel. The inner face (23), is indicated by a mark (22) visible through the transparent portion of the introducer (21). In this way the operator can easily orient the applicator and clamp correctly. An indication mark (26) on the proximal end (27) of the plunger (9) may also be used to identify the orientation of the clamp.

Figure 4A:
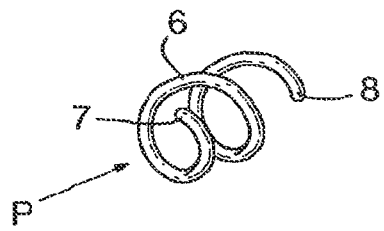
Figure 4B:
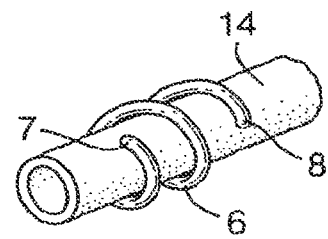
Figure 4C:
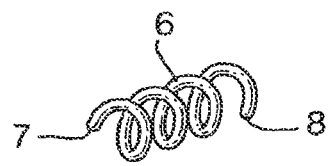
Figure 4D:
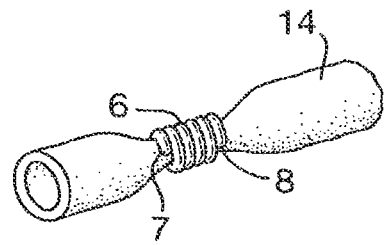
Figure 4E:
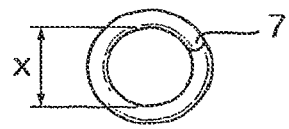
Figure 5A:
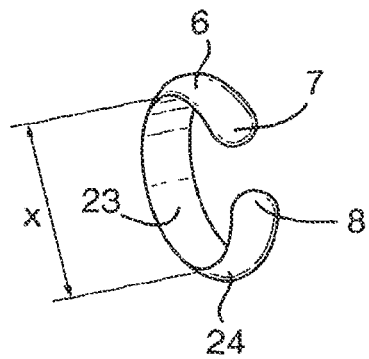
Figure 5B:
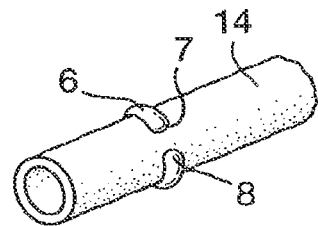
Figure 5C:
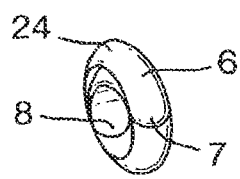
Figure 5D:
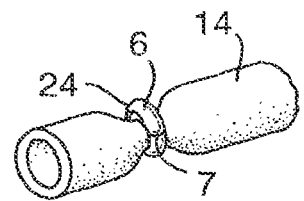

In each case the third form of the clamp, the form within the inner chamber of the applicator, is a linearised version of the first form. In each illustration (7) is the proximal end of the clamp (6), and (8) is the distal end. The internal diameter is indicated at "x". A blood vessel is illustrated at (14). The second form (4a) is a helical form where the proximal (7) and distal (8) ends of the clamp overlap side by side when placed over the blood vessel (14). Above the transition temperature of the shape memory material the clamp changes to the second form (4c) which is a tight helical form (4c) which reduces the internal diameter (x) and clamps the blood vessel closed. FIG. 4e shows an end on view from P. The proximal end is visible at (7) and the internal diameter is shown at (x).

FIGS. 5a-5d illustrate a clamp which is an open ring or "C" shaped. The clamp has an inner face (23) directed towards the blood vessel (14) and outer face (24) directed away from the blood vessel. The proximal (7) and distal (8) ends are radiused to allow easier passage around the blood vessel (14) during installation. The proximal (7) and distal (8) ends of the clamp (6) do not meet in the second form. Above the transition temperature of the shape memory material the clamp (6) changes to the second form (5c) which is a tight spiral form in which the proximal and distal ends of the clamp pass over and under each other, reducing the internal diameter of the clamp and closing the blood vessel.

Figure 6A:
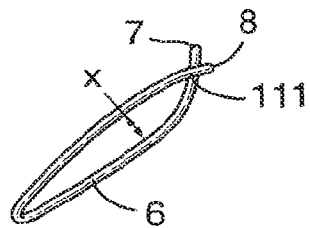
Figure 6B:
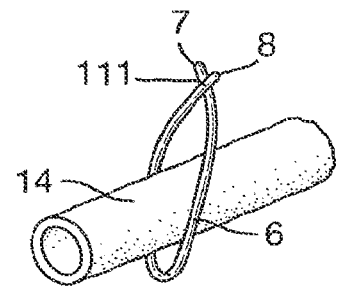
Figure 6C:
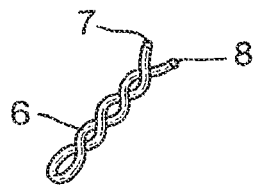
Figure 6D:
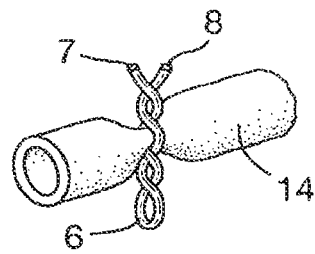

FIGS. 6a and 6b illustrate a further wire form of the clamp. In this form the second form is of a hairpin shape, in which the proximal (7) and distal (8) ends cross over (111). In the second form the hairpin forms a tight twisted pair, trapping the blood vessel (14) and clamping it closed (FIGS. 6c and 6d).

Figure 7A:
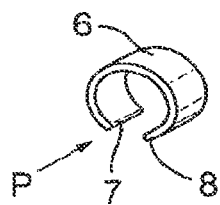
Figure 7B:
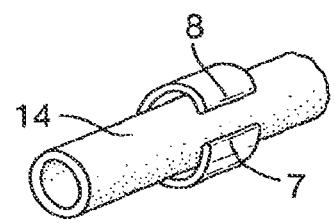
Figure 7C:
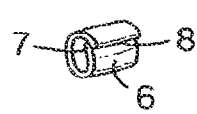
Figure 7D:
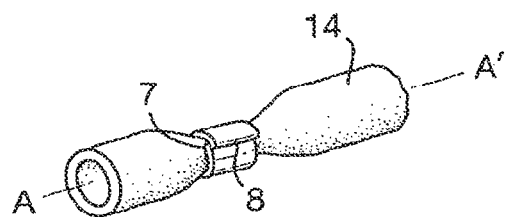
Figure 7E:
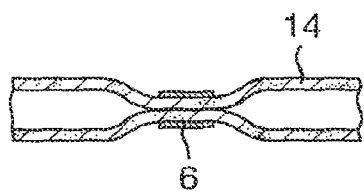
Figure 7F:
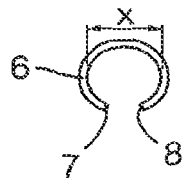

FIGS. 7a-7f illustrate a cylindrical form of the clamp, which has a proximal (7) and distal (8) end. The clamp has an outer face (24) directed away from the blood vessel and an inner face (23) directed towards the blood vessel. Above the transition temperature of the shape memory material the clamp (6) changes to the second form (7c) which is a spiral form in which the proximal and distal ends of the clamp pass over and under each other, reducing the internal diameter of the clamp and closing the blood vessel. FIG. 7e shows a cross section along A-A' showing the blood vessel (14) closed at (112) by the clamp (6).

FIG. 8 illustrates a further embodiment of the clamp. The clamp (generally 71) has a proximal end (77) and a distal end (78). The clamp comprises a resistive heating element (72) with terminal contacts (76), the heating element may, for example, be applied to either outer (24) or inner (23) faces of the clamp. The heating element is connected to an electrical circuit (generally 73) comprising a power supply (74) and a switch (75). The electrical circuit connects to the heating element (76) via contacts (79). Typically electric power is delivered to the contacts (76) through the applicator (not shown in this figure). Typically the power is delivered through the plunger. Delivering the power through the reversible engagement means allows the connection to remain in place during manipulation and only be broken once the clamp is ejected from the plunger.

FIG. 9 illustrates a further embodiment of the applicator. The applicator (generally 81) has housing (generally at 95) with an inner chamber (85) and comprises a tubular member (82) acting as an introducer. The tubular member has a proximal end (83) and distal end (84) and a lumen forming the inner chamber (85). A moving means in the form of a plunger (89) is moveable within the lumen (85) and is of sufficient length to move the clamp (6) out of the distal end of the tubular member (84). The plunger has a proximal end (86) and a distal end (87). At the distal end of the plunger is a means (88) for reversibly engaging the proximal end (7) of the clamp (6). In the case illustrated, the reversible engagement means is a slot (90) into which the proximal end (7) of the clamp (6) fits. The proximal end (7) of the clamp (6) is held within the slot and can be moved in and out of the distal end (84) of the applicator by manipulation of the plunger (89) whose proximal end (86) projects beyond the proximal end of the tubular member (83). The clamp (6) in its third form, tends to return to the first form, but is prevented from doing so by the inner wall (93) of the tubular member. For this reason the clamp in the third form in the illustration has a slight curve. The direction the clamp will bend once urged from the tubular member, is indicated by a mark (94) on the proximal end (86) of the plunger (89). An ejection means in the form of a rod (91) passes through the long axis of the plunger (89) and is operable to eject the clamp (6) from the slot (90) by applying pressure to the proximal end (92). A locking means (100) in the form of a removable pin (101) passes through the housing (87), plunger (89) and ejection means (91), thereby preventing accidental release of the clamp (6) until required.

Installation of the Clamp on a Vein

Degassed fluid such as normal saline is introduced into the area immediately surrounding the vein. The fluid serves to aid dissection of the vein away from surrounding tissue and create a path of low resistance around the vein. The degassed fluid provides a good contrast against which to visualise both the clamp and the vein to which it is to be attached. The fluid may also be used to deliver local anaesthetic. The distal end of the applicator penetrates the skin and is brought into close proximity with the vein. The clamp, which is in the third form inside the applicator is then urged out of the distal end of the inner chamber. As it exits the inner chamber and is no longer constrained, it returns to the first form, and begins to encircle the vein. The surgical clamp may then be withdrawn or it may serve as a conduit for addition or removal of saline. The clamp is then warmed to a temperature above the transition temperature of the shape memory material and transforms to the second form, completely encircling the vein and constricting it to close the lumen of the vein. Since the clamp is now in the stable, Austenitic form the clamp remains permanently in place.

In one approach the transition temperature of the shape memory material is 5 below body temperature. The immediate area of the vein is perfused with a cooled fluid. When the clamp, is urged from the distal end of the applicator it remains cool and below the transition temperature of the shape memory material. This aids manipulation as it leaves the applicator and returns to the first form in a controlled manner, where it encircles the structure under ultrasound guidance. Once the clamp is in place around the vein, the cooled fluid is removed or additional warmed fluid may be flushed through to warm the clamp above the transition temperature of the shape memory material. The clamp then transforms to the second form completely encircling the vein and constricting it to close the lumen.

In a further approach the transition temperature of the shape memory material is above body temperature. When the clamp, is urged from the applicator it remains at approximately body temperature and therefore below the transition temperature of the shape memory material. As the clamp leaves the applicator it returns to the first form and encircles the vein under ultrasound guidance. Once the clamp is in place, it is warmed above its transition temperature, for example by replacing the fluid surrounding the site with fluid above the transition temperature of the shape memory material. The clamp then transforms to the second form, constricting the vein and closing the lumen. Using this approach, control of the temperature at the site during clamp placement is less critical When using clamps comprising a heating means, the dissection of the vein and flooding with degassed normal saline may be carried out as above. The saline need not be heated or cooled. The distal end of the applicator penetrates the body wall and is brought into close proximity with the vein. The clamp, which is in the third form inside the applicator chamber and engaged by the plunger, is then urged out of the distal end of the applicator and can be adjusted in position by manipulation of the plunger. As the clamp leaves the applicator and is no longer constrained by the wall, it returns to the first form, and encircles the vein, but remains attached to the plunger. Adjustment of position is be made at this point under ultrasound guidance. Once happy with the position, power is connected to the heating element by operating the switch, the clamp heats up and changes to the second form constricting the blood vessel and closing the lumen. The eject means is then operated, releasing the clamp and the applicator can them be withdraw.

The invention claimed is:

1. An applicator for a surgical clamp (1) for clamping a blood vessel (14) comprising:
 a tubular housing (2), said tubular housing (2) having a proximal end (3), a distal end (4), and an inner lumen (5) having an opening on a distally facing surface at the distal end (4) of the tubular housing (2);

a surgical clamp (6) having a proximal end (7) and a distal end (8) within the lumen (5); and a plunger (9) configured to move the surgical clamp (6) out of the opening;

the surgical clamp (6) comprising a temperature sensitive shape memory material and capable of assuming:

a first, curved form in which the clamp (6) is shaped to partially encircle a blood vessel (14);

a second form in which the clamp (6) is shaped to substantially completely encircle the blood vessel (14) and to constrict the blood vessel (14) and thereby close the blood vessel (14); and a third, linearized form derived from the first form by resilient deformation of the clamp (6) in the first form and adoptable within the lumen (5), wherein the clamp (6) is induced to change from the third form to the first form as the clamp (6) leaves the opening, and from the first form to the second form on exposure to a temperature above the transition temperature of the shape memory material.

2. The applicator according to claim 1 wherein the plunger (9) releasably engages the clamp (6).

3. The applicator according to claim 1 comprising an indication (26) identifying a direction in which the clamp (6) will curve while being urged out of the opening.

4. The applicator according to claim 1 comprising a means (100) for preventing the clamp (6) from being moved from the lumen (5).

5. The applicator according to claim 1 in which the surgical clamp (6) in the first, curved form is a ring shape, a "U", "C" or "J" shape, a closed cylinder, or an open cylinder in which the proximal (7) and the distal (8) ends of the clamp (6) do not meet or is a spiral or helical shape.

6. The applicator according to claim 1 in which a distance between the proximal end (7) and the distal end (8) of the clamp (6) in the first, curved form, measured as the shortest distance between the proximal and distal extremities of the clamp (6), is less than a diameter of the vessel upon which the clamp is to be placed.

7. The applicator according to claim 1 in which the proximal end (7) and the distal end (8) of the clamp (6) approximately meet or overlap in the first form.

8. The applicator according to claim 1 in which the distal end (4) of the tubular housing (2) is formed into a point or blade to aid tissue penetration.

9. The applicator according to claim 1 wherein the plunger (9) is configured to urge the surgical clamp (6) out of the opening by abutting, and moving, the surgical clamp (6) distally within the inner lumen (5), to guide the distal end (8) of the surgical clamp (6) around the blood vessel (14), as the surgical clamp (6) begins to return to the first, curved form.

10. A method of clamping a blood vessel in the body of a subject, the method comprising the steps of:

(a) providing an applicator comprising:

a tubular housing (2), said tubular housing (2) having a proximal end (3), a distal end (4), and an inner lumen (5) having an opening on a distally facing surface at the distal end (4) of the tubular housing (2);

a surgical clamp (6) having a proximal end (7) and a distal end (8) within the lumen (5); and a plunger (9) configured to move the surgical clamp (6) out of the opening;

the surgical clamp (6) comprising a temperature sensitive shape memory material and capable of assuming:

a first, curved form in which the clamp (6) is shaped to partially encircle a blood vessel (14);

a second form shaped to substantially completely encircle said blood vessel (14) and to constrict the blood vessel (14) and thereby close the blood vessel (14), the clamp (6) configured to change from the first form to the second form above the transition temperature of the shape memory material, and a third, linearized form derived from the first form by resilient deformation of the clamp (6) in the first form, the clamp (6) being provided in the applicator in the third form;

(b) applying the clamp (6) to the blood vessel (14) by moving the plunger (9) distally to urge the clamp (6) from the opening, whilst allowing the clamp (6) to return to the first, curved form as the clamp (6) leaves the opening and guiding the distal end (8) of the surgical clamp (6) around the blood vessel (14); and (c) raising the temperature of the shape memory material to a temperature at which the shape memory material changes from the first form to the second form, thereby clamping said vessel (14).

11. The method according to claim 10 wherein a fluid is provided to bathe the blood vessel.

12. The method according to claim 11 wherein the fluid is cooled to a temperature below 37 C.

13. The method according to claim 11 wherein the fluid is degassed.

14. The method according to claim 10 wherein the temperature of the shape memory material is raised to a temperature at which the shape memory material changes to the second form by exposure to the subject's body.

15. The method according to claim 10 wherein the progress is to be followed by ultrasound.

16. An applicator for a surgical clamp (1) for clamping a blood vessel comprising:

a tubular housing (2), said tubular housing (2) having a proximal end (3), a distal end (4), and an inner lumen (5), the inner lumen (5) defining a longitudinal axis of the tubular housing (2), the inner lumen (5) having an opening at a distal end thereof, the opening spanning across the longitudinal axis;

a surgical clamp (6) having a proximal end (7) and a distal end (8), the surgical clamp (6) located linearly within the lumen (5) along the longitudinal axis; and a rod (9) within the lumen (5), the rod (9) configured to move longitudinally within the lumen (5) to distally move the surgical clamp (6) along the longitudinal axis and out of the opening at the distal end of the lumen (5);

wherein the surgical clamp (6) comprises a temperature sensitive shape memory material that assumes:

a first form in which the clamp (6) is shaped to partially encircle a blood vessel (14);

a second form in which the clamp (6) is shaped to substantially completely encircle the blood vessel (14) and to constrict the blood vessel (14), thereby closing the blood vessel (14); and a third form derived from the first form by resilient deformation of the clamp (6) in the first form, the resilient deformation making the clamp (6) conform to a shape of the lumen (5), lying straight along the longitudinal axis, and being located completely within the lumen (5), wherein the clamp (6) is induced to change from the third form to the first form as the distal end (8) of the clamp (6) longitudinally leaves the distal end of the lumen (5), and is induced to change from the first form to the second form on exposure to a temperature above the transition temperature of the shape memory material.

17. The applicator according to claim 16 wherein the clamp (6), configured to change from the third form to the first form, as the clamp (6) longitudinally leaves the distal end of the lumen, is configured to relax from a linear form to a martensitic form.

18. The applicator according to claim 16 wherein the rod (9), configured to move the surgical clamp (6) longitudinally out of the opening at the distal end of the lumen (5), is configured to abut the surgical clamp (6) within the lumen (5), to longitudinally translate the surgical clamp (6) out of the opening at the distal end of the lumen (5).

19. The applicator according to claim 16 further comprising a tab (100) releasably attached to, and extending at least partially laterally from, the rod (9), the tab (100) configured to prevent the rod (9) from abutting a proximal end (7) of the surgical clamp (6), and from longitudinally translating the surgical clamp (6) distally along the lumen (5).

20. The applicator according to claim 16 wherein the distal end (4) of the tubular housing (2) is formed into a point or blade to aid tissue penetration.

\* \* \* \* \*